United States Patent [19]
Wagers et al.

[11] 3,974,464
[45] Aug. 10, 1976

[54] ACOUSTIC RIDGE WAVEGUIDE

[75] Inventors: Robert S. Wagers, Richardson; Clinton S. Hartmann, Dallas, both of Tex.

[73] Assignee: Texas Instruments Incorporated, Dallas, Tex.

[22] Filed: Mar. 15, 1974

[21] Appl. No.: 451,718

[52] U.S. Cl. .............................. 333/30 R; 310/8.2; 310/9.8; 333/72
[51] Int. Cl.² ..................... H03H 9/26; H03H 9/30; H03H 9/32; H01L 41/10
[58] Field of Search ................ 333/30 R, 72; 310/8, 310/8.1, 9.5, 9.6, 9.7, 9.8; 331/107

[56] References Cited
OTHER PUBLICATIONS

Lagasse et al., "Acoustic Surface Waveguides–Analysis and Assessment," in IEEE Trans. on Microwave Theory and Techniques, vol. MTT21, No. 4, Apr. 1973, pp. 225–235.

Mason et al., "Electronics Letters," 15, July 1971, vol. 7, No. 14, pp. 395–397.

*Primary Examiner*—Alfred E. Smith
*Assistant Examiner*—Marvin Nussbaum
*Attorney, Agent, or Firm*—Harold Levine; James T. Comfort; William E. Hiller

[57] ABSTRACT

An improved acoustic waveguide structure which comprises a ridge waveguide disposed in a horizontal direction extending outwardly from a substrate. The horizontal orientation of the waveguide which is in the form of a ledge results in particle motion of the ledge predominantly normal to the substrate plane with the largest motion at the free edge of the ledge and almost no motion in the substrate, thereby permitting a plurality of such structures to be densely packed on a common substrate.

9 Claims, 19 Drawing Figures

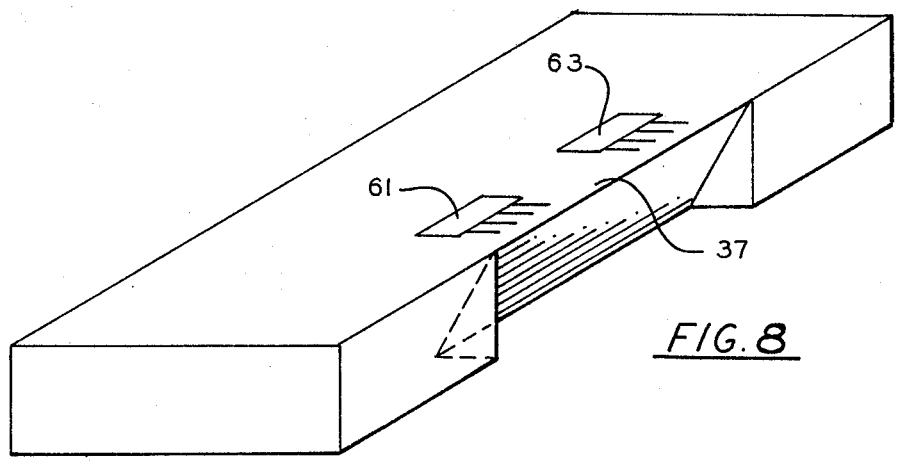
FIG. 8
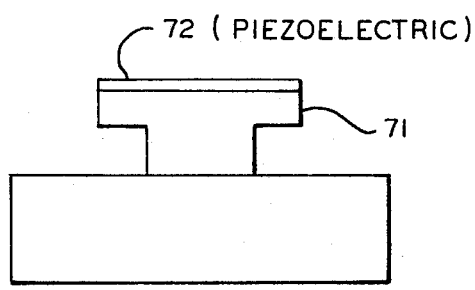
FIG. 10A
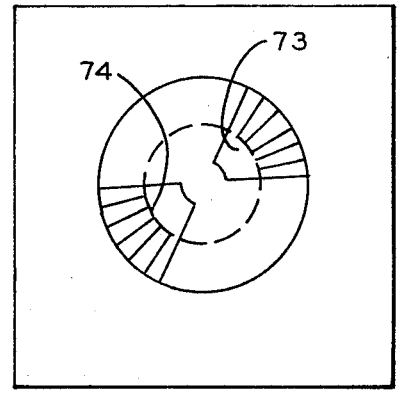
FIG. 10B
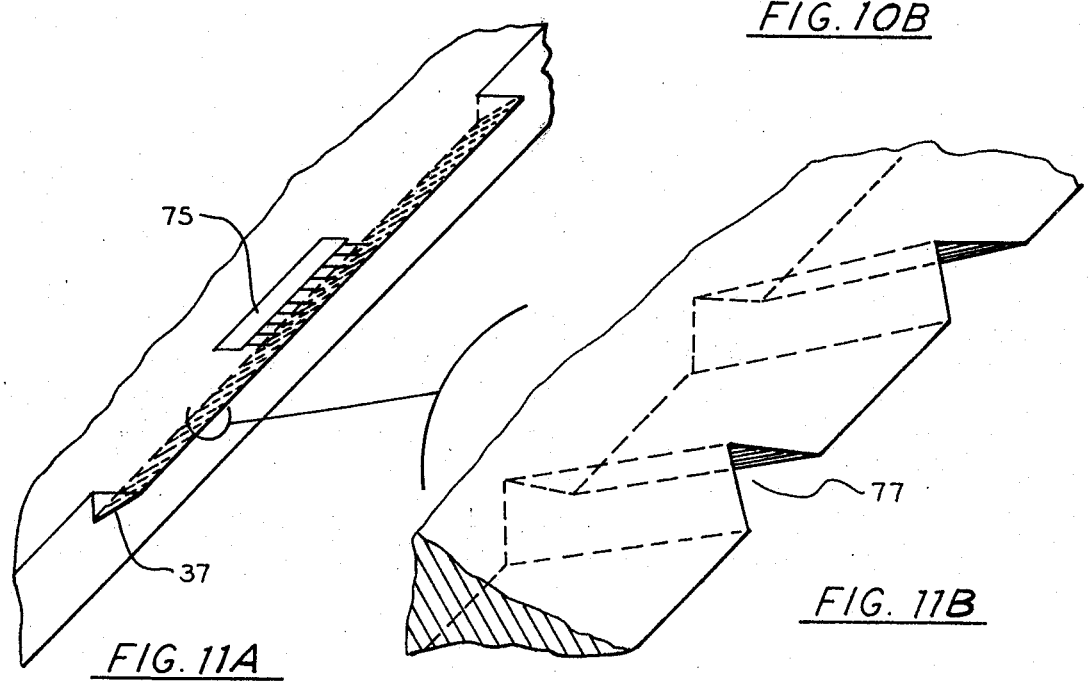
FIG. 11A
FIG. 11B

INPUT
OUTPUT

ACOUSTIC RIDGE WAVEGUIDE

BACKGROUND OF THE INVENTION

This invention relates to acoustic waveguides in general and more particularly to an improved type of waveguide which permits greater packing densities and other advantages.

Surface wave acoustic devices are gaining widespread use as filters, delay lines and the like. In particular, in frequency ranges between 10 mhz and 1 ghz, devices which are compact and provide numerous advantages over inductive-capacitive type filters and tuned electromagnetic waveguides are possible. This results directly from the fact that acoustic waves travel at a much slower speed than electromagnetic waves and thus, the size of a structure can be correspondingly smaller in the order of $10^5$.

When used in filtering applications these devices generally comprise a piezoelectric substrate on which are deposited two spaced transducers. The most common type of transducer used is what is known as the interdigital transducer wherein a plurality of fingers extend from the transducer pads on each side of the substrate and have overlapping portions. Electric fields created between the overlapping fingers of the transducer excite the piezoelectric material to generate the surface waves. Also used are what are known as grating mode transducers in which a grating of fingers coacts with a ground plane in much the same manner.

These conventional type waveguides where the waveguide is in the form of a plate, have waves therein which are referred to as Rayleigh modes. These conventional surface waves are subject to loss of energy due to diffraction which necessitates the use of acoustic beams that are many wave lengths wide. Such an arrangement offers certain disadvantages, particularly when it is desired to densely pack a plurality of waveguides.

To overcome some of these problems, waveguides which propagate in the lowest order anti-symmetric flexural mode, have been developed. Generally, the proposed waveguides have been vertically oriented structures such as that illustrated by FIG. 1. Considerable theoretical analysis has been performed on the performance of such a waveguide. Its dispersion as a function of guide cross sectional geometry has been computed as described in an article by P. E. Lagasse, I. M. Mason and E. A. Ash, entitled "Acoustic-Surface Waveguides—Analysis and Assessment," IEEE Trans MTT 21 No. 4, 225–235 (April, 1973), and in another article by R. Burridge and E. J. Sabina entitled "The Propagation of Elastic-Surface Waves Guided by Ridges," Proc. R. Soc. Lond. A. 330 pps. 417–441 (1972). The deformation associated with the different modes that the guide supports have been studied in the Burridge et al. article above and also in an article by C. C. Tu and G. W. Farnell entitled "Flexural Mode of Ridge Guides for Elastic Surface Waves," Elec Lett. 8 No. 3 pps. 68–69, (Feb. 10, 1972). In the last mentioned article, the field pattern penetration into the substrate was also presented.

In waveguides of this nature, the most tightly confined mode has a ridge structure as illustrated by FIG. 2A. The computer generated flexure illustrated by that figure shows that a substrate is virtually undisturbed by the presence of the mode in the guide. It is the property of the guide that makes it especially important since it leads to the possibility of a high density of non-interacting acoustic channels adjacent to each other on a common substrate. The graph of FIG. 2C illustrates the typical dispersion of this mode, i.e., the lowest order anti-symmetrical flexural mode is illustrated by the curve 11. The fact that the velocity of this mode can be very low is desirable in achieving long time delays. However, the dispersion evident in the lower branch is not desirable unless controllable.

The other category of mode guided by the ridge is the modified form of the Rayleigh wave. When a ridge is present on a half space, the Rayleigh mode becomes slowed down by the ridge and its amplitude falls off away from the ridge. This is illustrated by the computer generated flexural pattern of FIG. 2B. The inability of the guide to confine the energy of this mode makes it relatively uninteresting, particularly when it is noted that the guide has added dispersion for this mode. Typical dispersion for this mode is illustrated by the upper curve 13 of FIG. 2C.

Prior experimental efforts in making waveguides of this nature have taken basically two approaches. In one approach, thin vertically oriented rectangular ridges, such as that of FIG. 1, of aluminum have been machined. By its very nature, this approach did not permit fine geometries to be achieved and consequently the guides were limited to low frequency operation, i.e., less than 5 mhz. In addition, the nature of this type of approach results in a structure in which a high density of adjacent guides cannot be fabricated. Furthermore, the excitation of the guides presents severe problems. Since aluminum is not a piezoelectric material, a separate transduction means must be attached to the guide for the excitation of the modes. In the second approach which is disclosed in a paper by I. M. Mason, M. D. Motz and J. Chambers entitled "Wedge Waveguide Parametric Signal Processing," Proc. Ultrasonics Symposium, Boston, pps. 314–315, (October, 1972), one side of a piezoelectric substrate is lapped to produce a wedge shaped structure. The tip of the wedge then acts as the guiding ridge. This technique permits easy excitation of the mode since the substrate is piezoelectric. However, dispersion is difficult to control because of the craftsman-type construction method and a high density of guides is impossible to achieve. The main disadvantages of the prior art approaches are as follows:

1. Use of vertically oriented ridges does not lead to highly repeatable geometries and a high density of waveguides at VHF frequencies, unless substrates are used that admit to orientation dependent etching so that guide walls can be defined precisely by crystal planes. Presently, the material capability in this regard exists only for silicon which is a non-piezoelectric material. In turn, the use of silicon may lead to significant technological difficulties in the excitation of the required modes discussed below;

2. Even if highly precise repeatable guide geometries could be produced, the dispersion of the guide is not amenable to alteration, i.e., there is no parameter available for modification that will permit the dispersion in certain range of wave lengths to be flattened;

3. The motion of the guide is essentially parallel to the plane of the substrate and thus, not along the deformation direction of currently sputtered piezoelectric material.

Thus, it can be seen that although waveguides excited by tightly confined modes can offer distinct advantages, there is a need for an improved waveguide of this nature which does not suffer the above-noted drawbacks.

SUMMARY OF THE INVENTION

The present invention provides such a waveguide structure which avoids the above-noted disadvantages and discloses various ways of employing such a structure. This is accomplished in a waveguide structure which has a horizontal ledge extending from its attachment point at a substrate. With such a structure, the particle motion of the ledge is predominantly normal to the substrate plane. edge this arrangement, the motion is largest at the free ledge of the ledge whereas at the attached base of the ledge the motion is very slight and decays rapidly to zero within the substrate material. Thus, the acoustic energy in the ledge propagates along the ledge and is tightly confined to the ledge region. The disturbance extends into the substrate only a small fraction of the wavelength. Thus, tight packing of such waveguides is possible.

Various applications of the waveguide structure of the present invention are also disclosed. Its use in resonators, delay lines and filters is disclosed. Furthermore, the application of the ridge waveguide for generation non-linear interactions and an embodiment for such are also disclosed.

BRIEF DESCRIPTION OF THE DRAWINGS

FIG. 8 is a perspective view similar to FIG. 7, but showing a short circuited resonator configuration.

FIGS. 10A and 10B are respectively elevation and plan views of a closed loop resonator wherein the closed loop is obtained in a mechanical manner.

FIGS. 11A and 11B are perspective views illustrating a resonator having periodic reflectors on its ledge.

DETAILED DESCRIPTION OF THE PREFERRED EMBODIMENT

Figure 1:
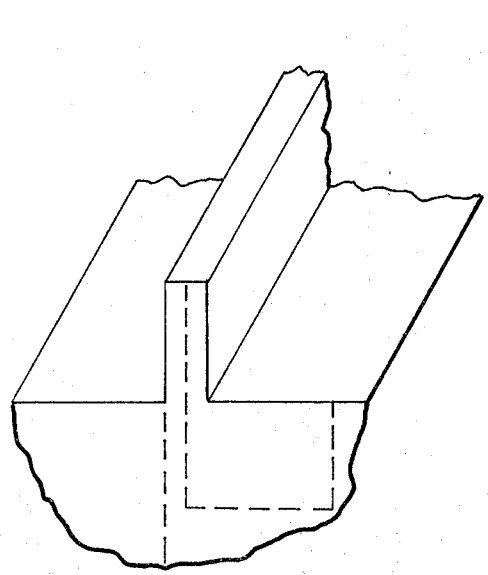
FIG. 1 is a vertical ridge waveguide such as those known in the prior art.
Figure 2A:
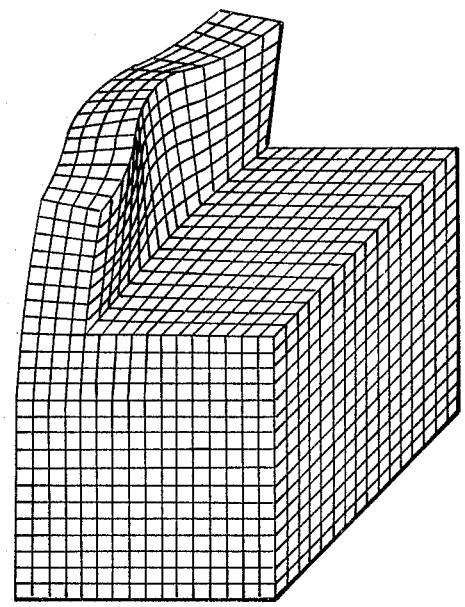
FIG. 2A is a computer generated flexure pattern for a ridge waveguide such as that of FIG. 1 guiding a tightly confined mode.
Figure 2C:
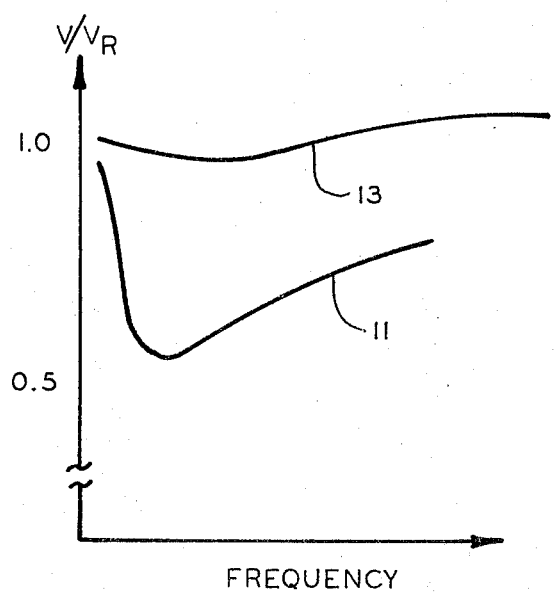
FIG. 2C is a graph illustrating the dispersion in the modes of FIGS. 2A and 2B.
Figure 2B:
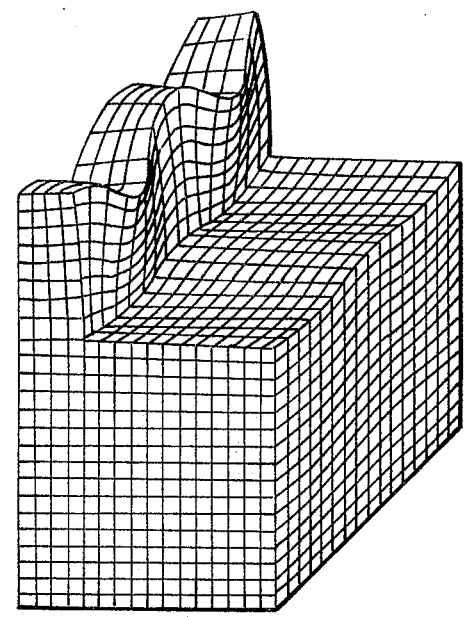
FIG. 2B is a similar illustration of a vertical ridge waveguide guiding a Rayleigh wave.
Figure 3:
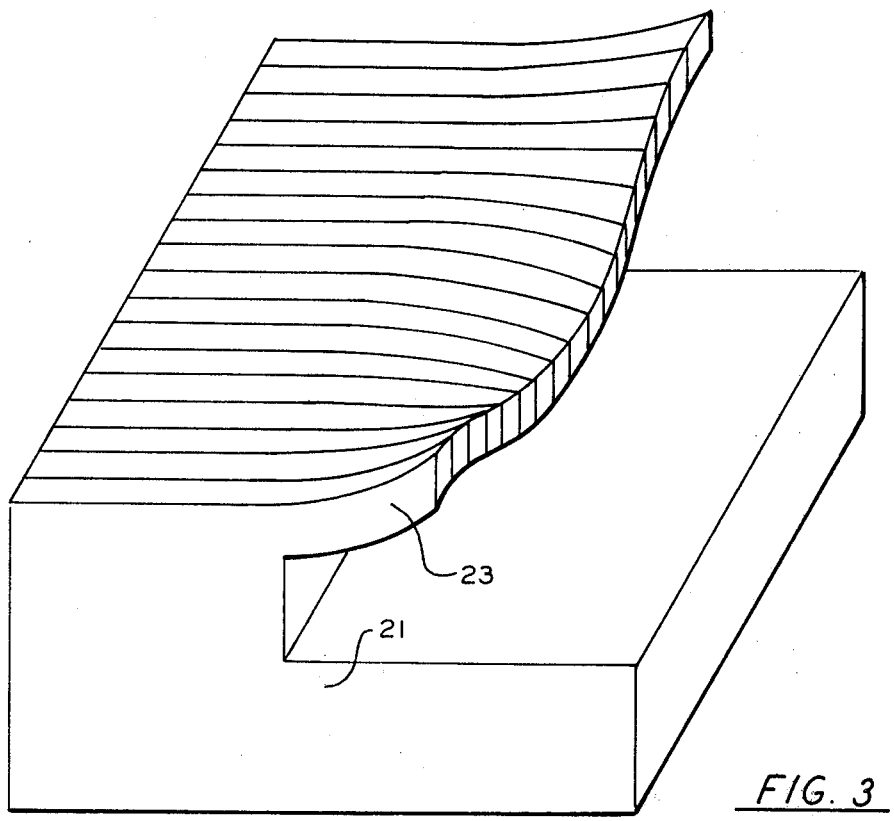
FIG. 3 is a perspective view illustrating one form of the horizontal ridge waveguide of the present invention.

FIG. 3 illustrates the waveguide structure of the present invention and the type of mode excited therein. Shown is a substrate 21 having a ledge 23 extending therefrom. As illustrated, an acoustic mode is exicted in the ledge causing it to flex up and down. The particle motion of the ledge is predominantly normal to the substrate plane. The drawing also illustrates in schematic form, the relative degree of motion at various positions in the ledge. As shown, at the free end of the ledge the motion is largest whereas at the attached base of the ledge the motion is very slight, and in the substrate material, the motion decays to zero rapidly. Thus, acoustic energy in the ledge propagates along the ledge and is tightly confined to the ledge region. Disturbances extend into the substrate only a small fraction of a wavelength. Typical dimensions of the ledge are on the order of ⅓ wavelength thick by 1 wavelength in lateral extent outwardly from the substrate.

Figure 4:
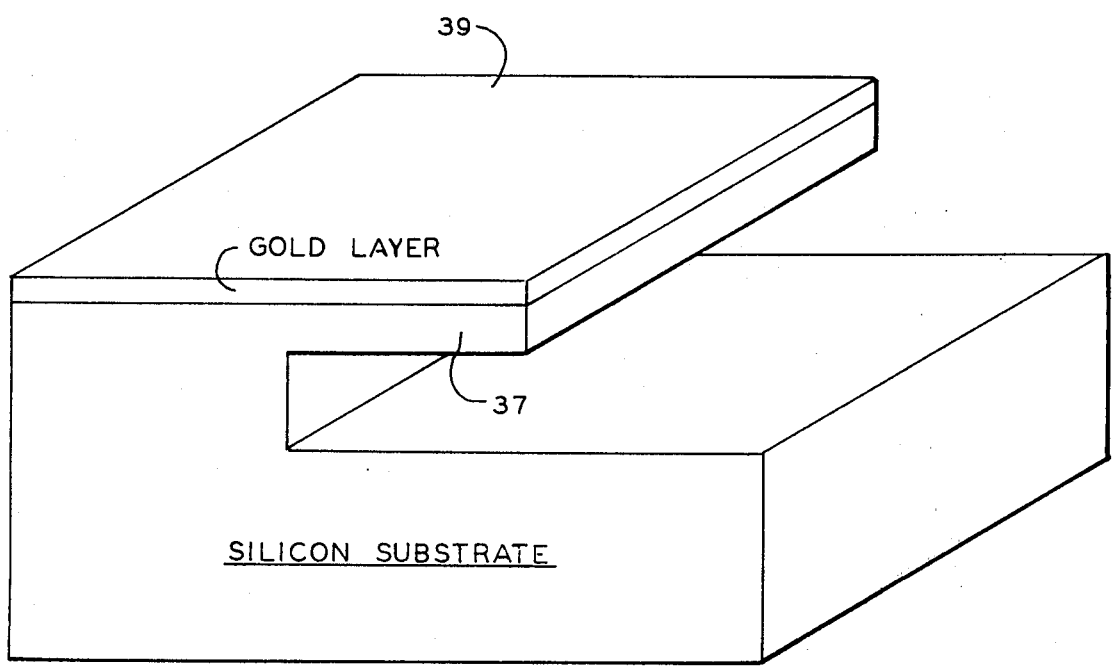
FIG. 4 is a perspective view of a ledge waveguide with a gold layer deposited thereon.
Figure 5:
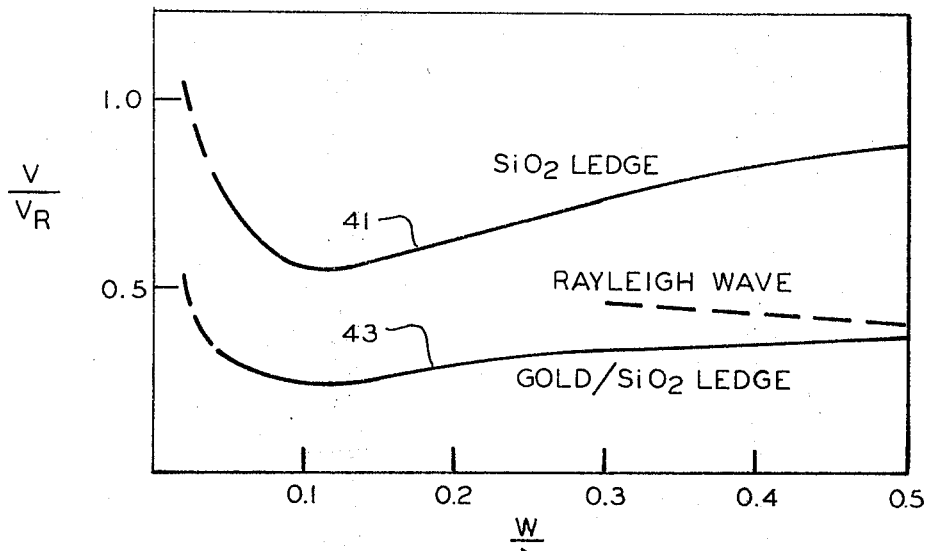
FIG. 5 is a graph illustrating the effects of the gold layer on the dispersion in the waveguide of FIG. 4.

The construction of the present invention also lends itself to controlled dispersion. Dispersion may be altered in a controlled manner through the evaporation of metals onto the exposed broad wall of the guide. This is illustrated by the embodiment of FIG. 4 which shows a single ledge of the type described in connection with FIG. 3. As illustrated, the silicon ridge 37 is mass loaded with a layer 39 of evaporated gold. The effect of such loading is illustrated by the curves of FIG. 5. The top curve 41 is for an $SiO_2$ guide having a thickness $w$ and a height $3w$. The bottom curve 43 is for a ledge which is one-half $SiO_2$ and one-half gold. The modification of the dispersion is evident from the curve. In the illustrated case, the velocity is slowed by a factor of approximately one-half while the fractional change in velocity is not altered appreciably. Also the example of FIG. 5 is for a guide of $SiO_2$ rather than silicon, but the results extend qualitatively to any guide with acoustic properties quite dissimilar from those of gold.

Figure 6:
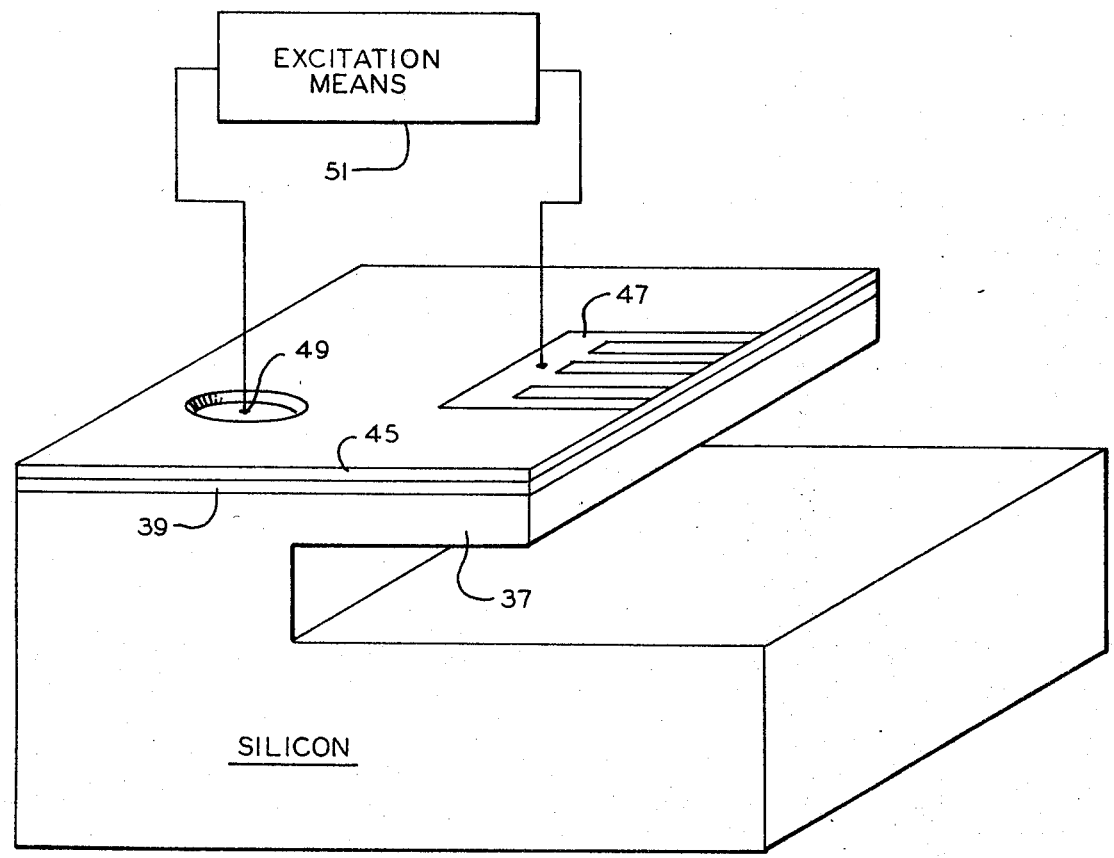
FIG. 6 is a view of the waveguide of FIG. 4 with a piezoelectric layer and a transducer deposited thereon.

The most important feature of the horizontal orientation is the potential for excitation of the guide. With the horizontal arrangement, the broad side of the guide is exposed and is lying in the plane of the substrate. This allows grating mode transducers to be fabricated directly on the broad wall of the guide over a sputtered piezoelectric film. An arrangement of this nature is illustrated by FIG. 6.

A ledge 37 is formed in silicon after which the ledge is mass-loaded with a layer 39 of gold as described above in connection with FIG. 4. The mass loading with gold not only slows the velocity of the mode leading to longer time delays but in addition, the gold serves as a ground electrode under the piezoelectric film and also acts to orient the film deposited on it, thus, ensuring high coupling. As illustrated, over the gold a piezoelectric layer 45 of ZnO is then deposited by sputtering, after which a grating mode transducer 47 is deposited over the ZnO film 45. An opening is made through the film 45 for attachment of a lead 49 to the ground plate 39 of gold. A suitable excitation means 51 may then be used to cause the grating mode transducer 47 to excite acoustic waves in the ledge 37.

Figure 7:
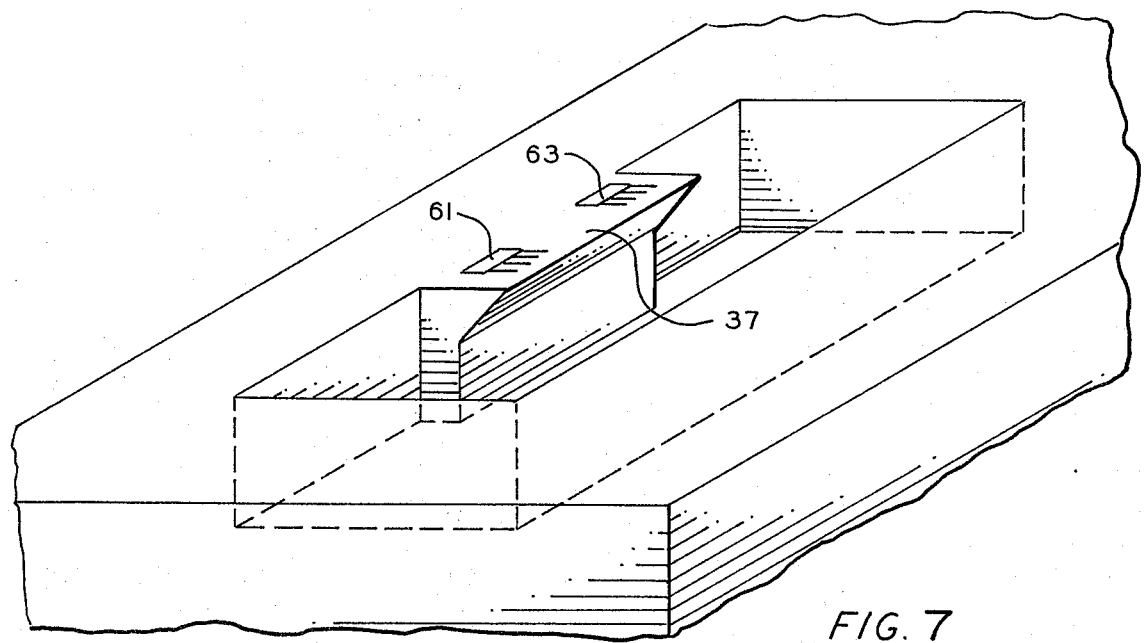
FIG. 7 is a perspective view illustrating a horizontal ridge waveguide configured as an open circuit resonator.

An application of the waveguide of the present invention as an open circuit resonator is illustrated by FIG. 7. In this embodiment, a ledge 37 is formed, which ledge is discontinuous at each end. A pair of transducers 61, 63 are deposited thereon in the manner described above. It should be noted that if a method of ledge formation such as that disclosed in copending application entitled "The Chemical Fabrication of Overhanging Ledges and Reflection gratings for Surface Wave Devices" Donald F. Weirauch, Ser. No. 429,475, filed Dec. 28, 1973, is used, the starting material is piezoelectric and transducers such as the transducers 61 and 63 shown in FIG. 7 can be directly deposited onto the ledge 37. In that case, the underside of the ledge can have a ground plane deposited thereon rather than using the gold and ZnO layers discussed above in connection with FIG. 6. The transducers 61 and 63 will be coupled to a source and a load in conventional fashion. This is not shown in order to maintain simplicity in FIG. 7. In the embodiment of FIG. 7, the acoustic mode is reflected from the discontinuity on the ledge and passes back and forth beneath the transducers. There is a synchronous frequency for which the round trip propagation between the two ends of the guides gives a phase shift of $2n\pi$, at which transmission between the ports becomes large, thus, achieving a filtering action. Thus, what has been shown is an open circuit resonator. Such resonators can be used as control elements to control the frequency of RF oscillators and may also be used as individual resonators in multi-pole band pass filters. Thus, a flexural ridge guided mode can be used as a means for trapping energy in a very small space to form a resonator. As noted above, the sizes involved for typical frequencies are generally much smaller than those obtainable with conventional components. Although illustrated using a wedge shaped waveguide which can be formed as described in the previously referenced patent application, other types of cross-sectional geometries such as discussed in connection with FIGS. 3, 4 and 6 may also be used. Dispersion is not particularly important in a resonator. Tight confinement, repeatability of fabrication and low propagation loss are the most important factors. In addition, the key feature needed in a resonator is that of providing means for feeding the signal back on itself to form a high Q standing wave resonator. One form of achieving this is the open circuit resonator of FIG. 7.

A second means of obtaining such operation is the short circuit resonator illustrated by FIG. 8. It should be noted at this point that the open circuit resonator and short circuit resonators of FIGS. 7 and 8 respectively are the analogs of open circuit or short circuit terminations in electrical waveguides. If the material velocity vector is defined as being equivalent to a voltage and the acoustic stress tensor as the analog of an electric current, then the simple structure in FIG. 7 is the analog of an electrical waveguide resonator where the ends are open circuited; that is the acoustic stress vanishes at the ends of the short waveguide section and the acoustic displacement obtains a maximum at these ends. The transducers shown are the equivalent of a pair of coupling loops in an electro-magnetic resonant waveguide cavity. Such a pair of coupling transducers are useful in a bandpass filter configuration with one transducer used for coupling into the resonator and the second transducer used for coupling back out of the same resonator structure. In a case where only a one port device is desired as in an RF oscillator, then only a single transducer is required.

The short circuited configuration of FIG. 8 differs from the configuration of FIG. 7 in that the opposite ends of the ledge of the waveguide respectively merge into the body of the substrate so as to be continuous therewith. Again, this is equivalent to a short circuited electro-magnetic waveguide and what has been said above in regard to transducers and couplings applies equally to this configuration. Either configuration may be used to obtain high Q resonant structures.

Figure 9:
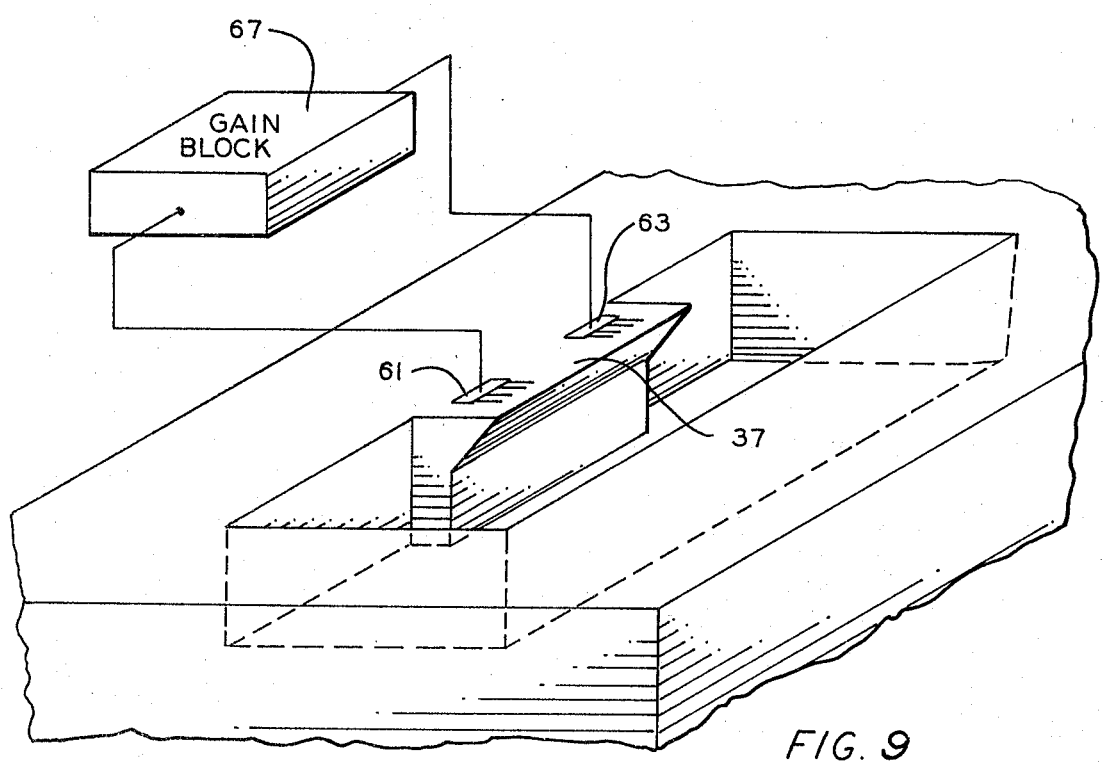
FIG. 9 is a perspective view similar to FIG. 7, but showing an electronically closed loop resonator.

FIG. 9 illustrates an electronically closed loop resonator. The structure is essentially the same as that of FIG. 7 with the primary difference being that a gain block 67 is used to couple the transducers 61 and 63. The signal from a transducer 61 is amplified in a gain block 67 such as an amplifier and then fed back to the transducer 63. The amplification is used to overcome propagation and transducer losses. The resonator shown on FIG. 9 is similar to the surface wave delay line resonators for use in UHF oscillators which are described in copending U.S. patent application Ser. No. 301,918 filed Oct. 30, 1972, now U.S. Pat. No. 3,868,595. In the present embodiment, it is desired to damp the signals which leak past the transducers such that spurious resonances do not occur but rather that the resonance is precisely controlled by the spacing between the two transducers. A major advantage of this resonator over previous structures is that the resonance can be more precisely controlled by a simple metallization pattern, i.e., by the spacing of the transducers, and that the Q of the resonator can be more easily controlled externally by varying the gain in the loop.

Another manner of obtaining a closed loop resonator is illustrated by the embodiment of FIGS. 10A and 10B. A cylindrical ledge 71 is formed in a silicon wafer in a suitable manner. A piezoelectric layer 72 and necessary loading and transducers 73, 74 are placed thereon in the manner described in connection with FIGS. 6 and 7. The transducers 73 and 74 shown in FIGS. 10A and 10B have radially extending fingers. In this case, the wave guiding structure forms a closed loop in the form of a circle. No reflection is required with the signal simply running around in a closed path.

FIGS. 11A and 11B illustrate another manner of obtaining resonance. As illustrated in FIG. 11A, a ledge 37 similar to that of FIG. 7 is formed upon which is placed a single transducer 75. The underside of the ledge 37 contains a plurality of indentations 77 which act as perturbations or reflectors. Although shown in detail in FIG. 11B as being formed by cut-outs or notches on the bottom side of the ledge 37, other forms of perturbations may also be used. This construction forms a periodic corrugation on the waveguide structure. As the acoustic waves encounter these perturbations, they will be reflected with the resonance being determined by the spacing of the perturbations. Another manner of obtaining reflectors to accomplish the same result is through the deposition on the ledge 37 of another material such as gold, zinc oxide or various other low loss acoustic materials and then the patterning of these materials, possibly during the same step as when forming the coupling transducers, to define reflector strips selectively positioned on the ledge 37. Such patterned zinc oxide structures have been shown to be very successful for similar resonators which operate using standard Rayleigh waves.

As noted above, the major advantage of the ridge waveguide in a resonant structure as compared to conventional structures using Rayleigh waves is primarily in its compactness which permits a large number of resonant structures to be built into a small area and also allows very compact bandpass filters and resonators for RF circuit applications to be constructed. The latter can be constructed as an integrated circuit bandpass filter.

The waveguides of the present invention are also applicable for use as delay lines and in particular lead to the ability to construct extremely long delay lines which take up very little room. Delay lines constructed using the waveguides of the present invention can be used as analog memory for such things as single line or frame storage for a television picture or as memory for use in correlation from one line to another in a television image. In addition, these waveguides have digital applications and are particularly useful in cases where extremely high speed digital data is used. They may also be used in other well-known delay line applications. For example, these devices can be used as a clutter reference for a radar or as a transmitter frequency reference for a radar system. The primary feature of the flexural acoustic guided wave for use in long delay lines is that the wave is tightly confined to a very small guide permitting a large number of guides to be packaged very closely together to obtain a very compact delay line and further that the high confinement possible in such waveguides means that there will be no cross talk between adjacent waveguides.

Since the waveguides cannot always be of a length sufficient to obtain the required delay, means must be provided for changing the direction of wave propagation in the guide on the surface. In a construction such as that described above in connection with FIG. 3, it may be possible to build in changes in direction. However, difficulties arise when using the type of wedge structure disclosed in the aforesaid co-pending U.S. patent application Ser. No. 429,475, filed Dec. 28, 1973 previously mentioned. Thus, in waveguides made according to such techniques, turning of corners in the waveguide structure is not practical.

Figure 12:
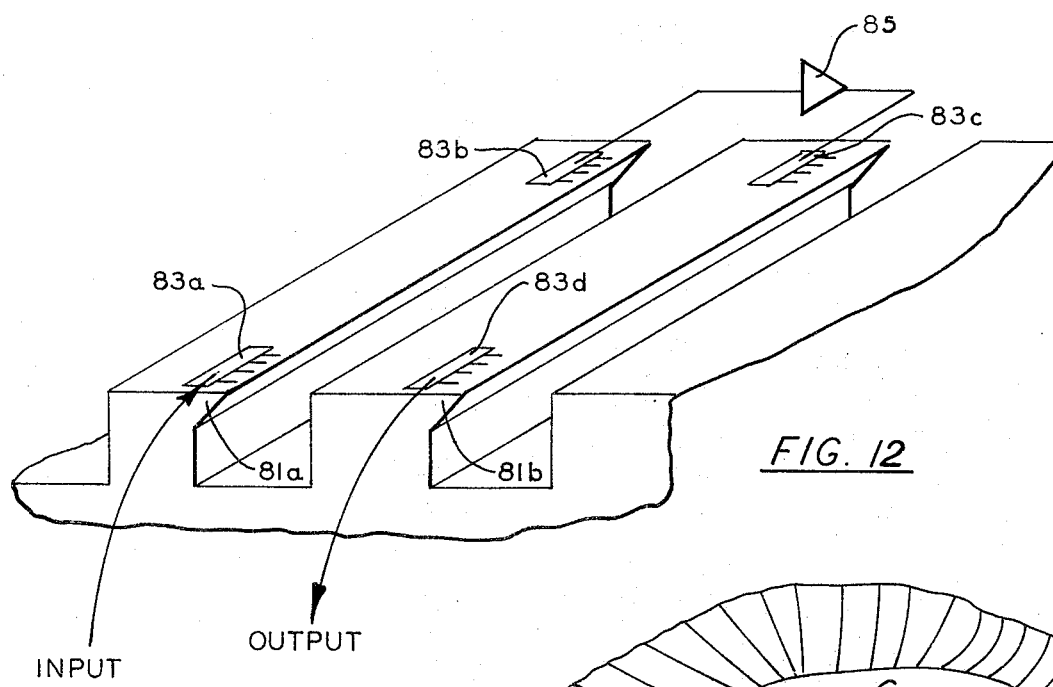
FIG. 12 is a perspective view illustrating the application of the horizontal waveguide of the present invention in a delay line using active regeneration and coupling between ridges.

FIG. 12 illustrates, however, one technique wherein such turning may be accomplished. A plurality of waveguides 81a and 81b are shown. The input is provided to the transducer 83a which excites the wave in the waveguide 81a. The transducer 83b converts the acoustic energy back to electrical energy which is then provided to a regeneration amplifier 85 whose output is coupled to the transducer 83c on the waveguide 81b. The acoustic wave generated by this transducer is then transmitted to the transducer 83d where it is again converted to electrical energy and may be provided as an output. Although only two passes through waveguides are shown in FIG. 12, it will be evident that as many as required may be used with regeneration amplifiers 85 coupling each succeeding pair of waveguides. The amplifier 85 may be integrated directly onto the substrate. This arrangement offers a further advantage in that each regeneration point coupling two waveguide structures may also be used as a tap, thus making information stored in the delay line accessible at many points.

Figure 13:
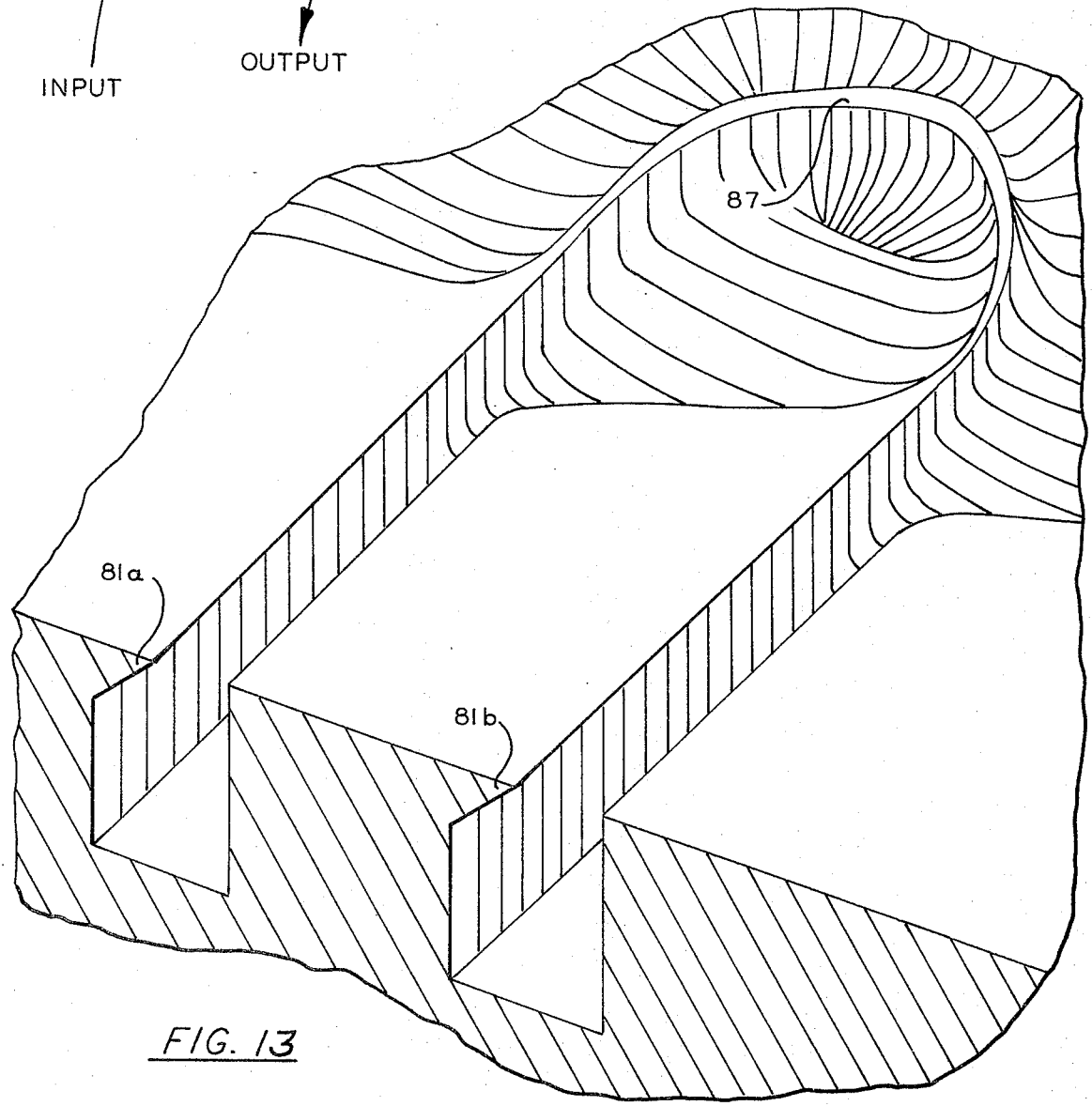
FIG. 13 is a perspective view of a delay line structure wherein coupling between ridges is done through a vertical ridge guide connecting loop.

Another manner of turning a corner is illustrated by FIG. 13. A illustrated, at the end where the waveguide 81a is coupled to the waveguide 81b, the structure is modified so that it goes from being a horizontal structure to a vertical structure 87. The vertical structure 87 is then used to turn the corner whereupon it is then changed back to a horizontal structure. The end portion can be fabricated with omnidirectional etching.

Although both the wedge type waveguide structure which can be made as described in the aforesaid co-pending application and the structure disclosed in connection with FIGS. 3, 4, and 6 can both be used in many applications, the wedge waveguide has features which make it preferable. In particular, it has better dispersion qualities. In long delay lines minimizing dispersion is quite important since dispersion tends to spread the R.F pulses over a longer time length and tends to round off sharp rising and falling wave forms. For example, consider a delay line with an nominal time delay $\tau$ at its center frequency and a fractional change in propagation velocity across its band width equal to $\Delta V/V$. Further, let $T_1$ be the time width of the smallest pulse which is desired to be transmitted faithfully through the delay line. The amount such as pulse will spread, designated $T_s$ is as follows:

$$t_s \simeq \tau \Delta V/V$$

If the condition is imposed that the amount of spread of the pulse be less than the width of the shortest pulse which must be passed, the following equation holds:

$$T_s < T_1$$

Combining these two equations the following is obtained:

$$T_1 > \tau \Delta V/V$$

or $$\Delta V/V < T_1/\tau$$

From this, the ratio of $\tau$ divided by $T_1$ can be recognized as the useful number of bits of information which may be stored in the guide and may be designed by $N$. From this, the dispersion across the band width of the delay line must satisfy the following condition:

$$\Delta V/V < 1/N$$

For most cases of practical interest, the number $N$ will range from between 100 and 100,000 thereby making the dispersion requirements extremely stringent. As a result, the only flexural guided mode which is of practical use for long delay lines is that which occurs in a wedge shaped waveguide. Such a waveguide must have a wedge that is taller than an acoustic wavelength at the lowest frequency of interest in order to achieve acceptably low dispersion characteristics such as those described in the Lagasse et al. article noted above.

While the wedge waveguide is the only structure which is nearly non-dispersive, the other geometries discussed above which do have high dispersion may be used in other types of applications such as in forming dispersive delay lines, which are used in radar systems and for pulse compression filters.

The wedge waveguide structure may also be used to build a class of filters referred to as transversal filters. These are filters that basically comprise a delay line wherein the signal passes under many taps which sample the signal at different time delay increments and the samples are then all summed. A large majority of the surface wave filters currently in use or under development are transversal filters in that both the input transducers and output transducers used in these filters comprise basically a plurality of small taps on a surface delay line which are used either to generate or detect a small portion of the total wave. Transversal filters are an extremely flexible class of filters which are used for such diverse applications as bandpass filters, pulse compression filters, phase coded correlators, frequency discriminators, and specialized filters which require unusual amplitude and/or phase responses, possibly in several different bandpass regions in a single filter. Transversal filters can be built using the non-dispersive delay lines described above with a plurality of multiple taps placed on the delay line structure to coincide with the desired impulse response of the filter.

Figure 14:
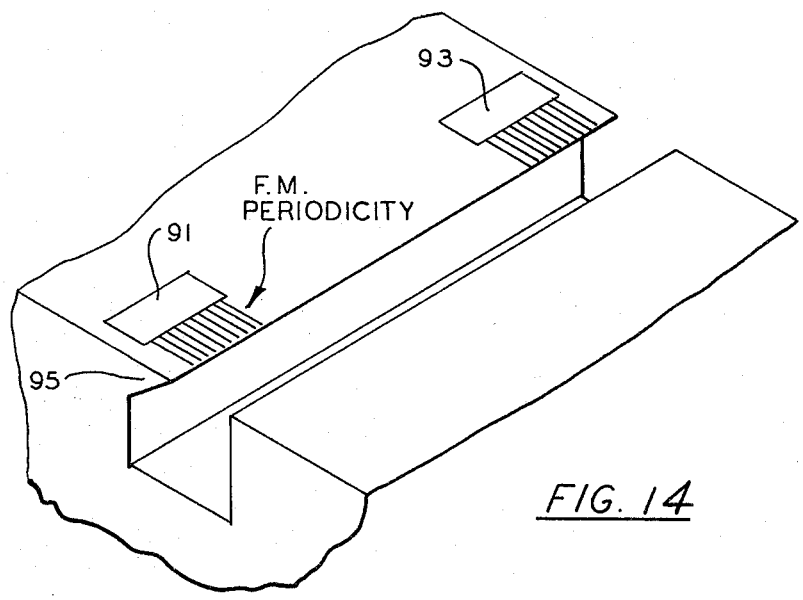
FIG. 14 is a perspective view illustrating the use of the ridge waveguide in a transverse filtering arrangement.

An example of such use is illustrated in FIG. 14. Here transducers 91 and 93 are deposited on the wedge shaped waveguide structure 95. The transducers 91 and 93 each have an FM periodicity. Such an arrangement is useful as a pulse compression filter for a radar system, for example. In principal, all surface wave devices now in existence can be constructed using the wedge or horizontal waveguide of the present invention and in particular, through the use of the wedge waveguide.

A further application of the flexural ridge guide is in its use for generation non-linear interactions. Non-linear acoustic correlators have been previously developed and disclosed for both surface wave devices and flexural ridge guided wave devices. For example, such is disclosed in an article by I. M. Mason and M. D. Motz and J. Chambers entitled "Wedge Waveguide Parametric Signal Processing" Proc. Ultrasonics Symposium, Boston, 314–315, (Oct., 1972). In general, non-linear interactions are not of particular interest for standard surface wave devices because extremely high power levels must be used before a sufficient power density is achieved to observe acoustic non-linearities that are large enough to be useful. However, with a ridge guided mode, the acoustic energy is confined to less than one wavelength whereas typical surface wave devices have this energy spread over a distance on the order of 100 wavelengths wide. Therefore, with the ridge waveguide, extremely high power densities may be easily achieved. This is particularly true in the wedge-shaped guide because the strain at the tip of the wedge becomes very large. This permits the flexural ridge guided mode to be used for non-linear interactions and in particular, for mixing applications where it is desired to obtain either the sum or difference of two frequencies of interest.

Figure 15:
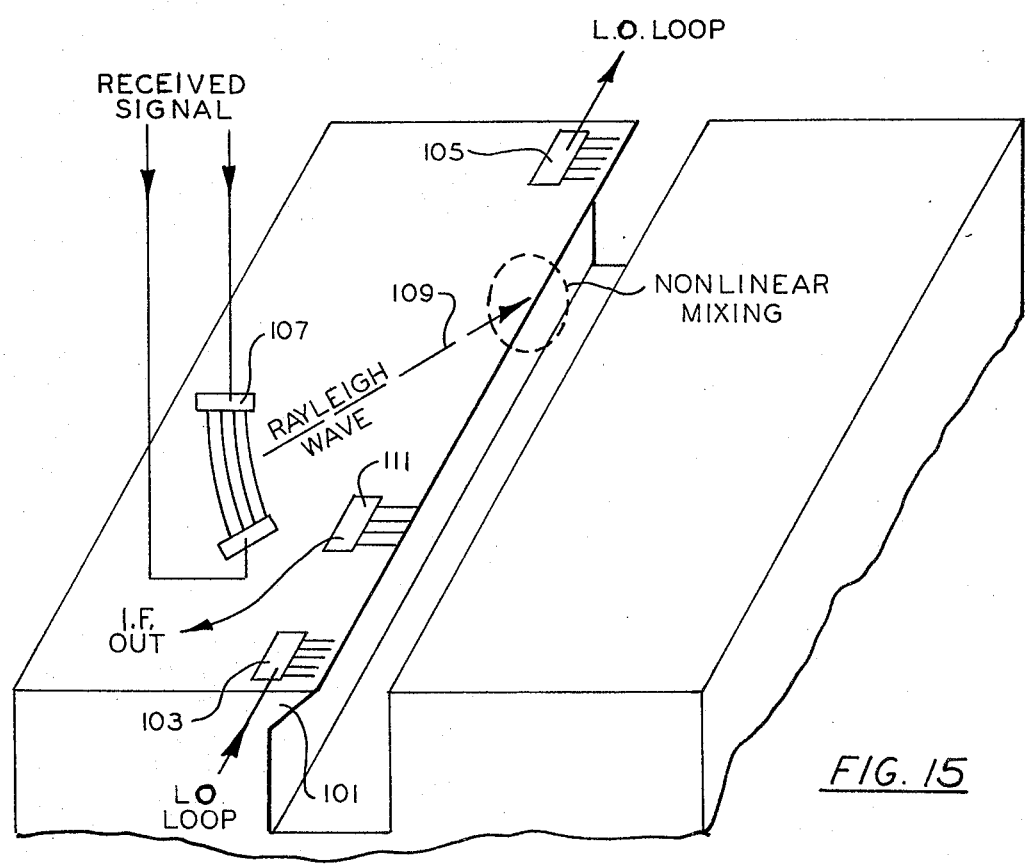
FIG. 15 is a perspective view illustrating the manner in which non-linear interaction may be obtained with a horizontal ridge guide such as that of the present invention.

Such an arrangement is shown in FIG. 15. Here, a long flexural mode delay line is used as a frequency controlling element for a feedback oscillator. A flexural ridge waveguide 101 is provided and has deposited on its ends transducers 103 and 105. The spacing between the transducer 103 and the transducer 105 is made much larger than the reciprocal of the band width of the transducers. Thus, there are many frequencies at which the oscillator can resonate. The particular frequency is chosen by a low Q external circuit. Thus, this could easily form the local oscillator for a receiver having equal channel spacings, for example, 100 KHZ. An interdigital transducer 107 is deposited on the top of the structure and is used to generate a Rayleigh wave in the direction of arrow 109. The surface wave so generated will be incident obliquely on the ridge in its center portion where the strain is large. The result will be such that the difference of the surface wave vector and the ridge guided mode wave vector correspond to the periodicity of an output transducer III placed on the center of the delay line and which operates at the desired IF frequency for the receiver application. The received signal in this case is transduced into a normal Rayleigh surface wave and simultaneously filtered by the input transducer. The output coupling electrode on the transducer III forms the IF filter for this particular device. With proper design, a device such as this can be used to provide a receiver front end having a reasonably low noise figure and a wide dynamic range. By installing a plurality of transducers 107 connected in parallel at appropriate angles, each corresponding to a different frequency, or one curved transducer as shown, a very simple tunable receiver where the only tuning required is the external tuning of the oscillator loop can be provided. Furthermore, an additional feature of this type of non-linear mixing is that, since propagating waves are involved, there is a wave vector selection as well as a frequency selection which must be satisfied and hence single-side band mixing is obtained, i.e., no images are present. A modification of the embodiment of FIG. 15 would be in the deposition of another broad band input transducer on the ridge guided delay line so that the input signal would be coupled into the delay line in the form of a ridge guided wave instead of a Rayleigh wave. The advantage of this configuration over the previous one would be increased efficiency and a more compact device. Its disadvantage is a more complex fabrication for the ridge guided structure and a wider necessary operating band width for the ridge guide.

Thus, an improved type of ridge waveguide and a plurality of applications therefor have been shown. Although specific embodiments have been illustrated and described it will be obvious to those skilled in the art that various modifications may be made without departing from the spirit of the invention which is intended to be limited solely by the appended claims.

What is claimed is:
1. An acoustic waveguide structure comprising:
   a substrate formed of a single crystal piezoelectric material and having a top surface lying in a horizontal plane; and
   a wedge-shaped horizontal ledge formed of said single crystal piezoelectric material extending laterally outwardly from said substrate and having a top surface coplanar with the top surface of said substrate.
2. An acoustic waveguide structure as set forth in claim 1, further including means operably associated with the top surface of said ledge for exciting acoustic waves therein.
3. An acoustic waveguide structure comprising:
   a substrate formed of a single crystal piezoelectric material and having a top surface lying in a horizontal plane; and
   a horizontal ledge formed of said single crystal piezoelectric material extending laterally outwardly from said substrate and having a top surface coplanar with the top surface of said substrate, said ledge being of the order of ⅓ wavelength thick and one wavelength in lateral extent outwardly from said substrate.
4. An acoustic waveguide structure comprising:

a substrate formed of single crystal silicon, said substrate having a top surface lying in a horizontal plane;
a wedge-shaped horizontal ledge extending laterally outwardly from said substrate and having a top surface coplanar with the top surface of said substrate; and
means operably associated with the top surface of said ledge for exciting acoustic waves therein.

5. An acoustic waveguide structure comprising:
a substrate formed of single crystal silicon, said substrate having a top surface lying in a horizontal plane;
a horizontal ledge formed of said single crystal silicon extending laterally outwardly from said substrate and having a top surface coplanar with the top surface of said substrate;
a metal layer deposited over the top surfaces of said silicon ledge and silicon substrate; and
means operably associated with the top surface of said ledge for exciting acoustic waves therein, said acoustic wave-exciting means comprising a piezoelectric layer over said metal layer and a transducer deposited on said piezoelectric layer so as to be disposed over said ledge.

6. An acoustic waveguide structure as set forth in claim 5, wherein said metal layer is gold and said piezoelectric layer is zinc oxide.

7. An acoustic waveguide structure comprising:
a substrate formed of single crystal silicon, said substrate having a top surface lying in a horizontal plane;
a horizontal ledge extending laterally outwardly from said substrate and having a top surface coplanar with the top surface of said substrate, said ledge being of the order of ⅓ wavelength thick and one wavelength in lateral extent outwardly from said substrate; and
means operably associated with the top surface of said ledge for exciting acoustic waves therein.

8. An acoustic waveguide structure comprising:
a substrate made of a material taken from the group consisting of single crystal silicon and single crystal piezoelectric material;
a ledge integral with said substrate and extending laterally outwardly with respect to a first surface of said substrate;
said ledge having a surface corresponding to and coplanar with a second surface of said substrate which is perpendicular to said first surface of said substrate; and
said surface of said ledge being contiguous with said second surface of said substrate along the extent of said ledge.

9. An acoustic waveguide structure comprising:
a substrate formed of single crystal silicon;
a ledge integral with said substrate and extending laterally outwardly with respect to a first surface of said substrate;
said ledge having a surface corresponding to and coplanar with a second surface of said substrate which is perpendicular to said first surface of said substrate;
said surface of said ledge being contiguous with said second surface of said substrate along the extent of said ledge; and
means operably associated with said surface of said ledge for exciting acoustic waves therein.

* * * * *